United States Patent [19]

Iwasaki et al.

[11] Patent Number: 4,851,421
[45] Date of Patent: Jul. 25, 1989

[54] BIOCIDAL FINE POWDER AND A SUSPENSION CONTAINING THE SAME

[75] Inventors: Tetsuji Iwasaki; Yasushi Kamihisa, both of Wakayma, Japan

[73] Assignee: Kao Corporation, Tokyo, Japan

[21] Appl. No.: 943,992

[22] Filed: Dec. 22, 1986

Related U.S. Application Data

[63] Continuation-in-part of Ser. No. 770,207, Aug. 28, 1985, Pat. No. 4,663,364.

[30] Foreign Application Priority Data

Sep. 5, 1984 [JP] Japan .................. 59-185889
Oct. 17, 1984 [JP] Japan .................. 59-218149

[51] Int. Cl.$^4$ .............................. A01N 25/02
[52] U.S. Cl. .................... 514/352; 514/417; 514/421; 514/425; 514/437; 514/941; 514/942; 514/943; 514/951; 514/952; 424/405; 424/489; 424/502
[58] Field of Search ............... 424/134, 131, 141, 143, 424/164, 405, 489, 502; 514/352, 417, 421, 425, 937, 941, 942, 943, 951, 952

[56] References Cited

U.S. PATENT DOCUMENTS

| | | | |
|---|---|---|---|
| 2,553,770 | 5/1951 | Kittleson | 514/417 |
| 2,658,016 | 11/1953 | Brown et al. | 424/164 |
| 3,157,486 | 11/1964 | Harrison et al. | 71/93 |
| 3,689,661 | 9/1972 | Braude et al. | 514/417 |
| 3,737,551 | 6/1973 | Karsten et al. | 514/483 |
| 3,920,807 | 11/1975 | Curry et al. | 424/46 |
| 4,663,364 | 5/1987 | Iwasaki et al. | 428/402 |
| 4,670,430 | 6/1987 | Imamura et al. | 514/188 |

FOREIGN PATENT DOCUMENTS

| | | |
|---|---|---|
| 0014503 | 3/1980 | European Pat. Off. . |
| 0067484 | 12/1982 | European Pat. Off. . |
| 454569 | 12/1927 | Fed. Rep. of Germany . |
| 558457 | 8/1923 | France . |
| 1026727 | 4/1953 | France . |
| 1061584 | 4/1954 | France . |
| 59-185889 | 5/1984 | Japan . |
| 59-218149 | 10/1984 | Japan . |
| 2030045 | 4/1980 | United Kingdom . |

OTHER PUBLICATIONS

Chemical Abstracts, vol. 96, No. 3, Jan. 18, 1982, p. 111, Abstract No. 16050j.

Pesticide Science, vol. 8, 1977, pp. 214–216, London, GB, MacQuillan et al.: "Effects of Particle Size and Active . . ."

W. Van Valkenburg, Pesticide Formulations, 1973, pp. 174–178, M. Dekker, Inc. New York, U.S.A.

*Primary Examiner*—John Kight
*Assistant Examiner*—Samuel A. Acquah
*Attorney, Agent, or Firm*—Oblon, Spivak, McClelland, Maier, Neustadt

[57] ABSTRACT

The invention relates to a biocidal fine powder with increased biocidal activity and an agricultural suspension containing the biocidal fine powder and an adjuvant selected from the group consisting of polyoxyalkylene-type nonionic surface active agents and polyoxyalkylene alkyl or alkylaryl ether phosphates or their salts.

6 Claims, No Drawings

BIOCIDAL FINE POWDER AND A SUSPENSION CONTAINING THE SAME

RELATED APPLICATIONS

This application is a continuation-in-part application of Application Ser. No. 770,207, filed Aug. 28, 1985, now U.S. Pat. No. 4,663,364.

BACKGROUND OF THE INVENTION

1. Field of the Invention:

This invention relates to a biocidal fine powder having a notably reinforced biological effect, to its manufacturing method and to a suspension for agricultural use containing the above powder.

2. Description of the Background:

Biocidal agents such as insecticides, germicides, herbicides and miticides are effectively insoluble in water. Therefore they are used in an aqueous fluid suspension.

As compared to an emulsion prepared by dissolving a biocidal agent in an organic solvent such as xylene or kerosene, a fluid suspension has advantages in terms of its storage, cost, environmental pollution and phytotoxicity to crops. In addition, a fluid suspension can be prepared even when there is no proper organic solvents for the biocidal agent. And, a fluid suspension is a form most suitable for spraying.

As described above, fluid suspensions of biocidal agents have several advantages and various studies have been carried out in order to improve their quality. Nevertheless, a fluid suspension of satisfactory quality has not yet been achieved because of caking and increased viscosity caused when it is stored over a prolonged period.

SUMMARY OF THE INVENTION

Accordingly, one object of the present invention is to provide a biocidal fine powder which has high biological effect and prolonged stability.

Another object of the invention is to provide a fluid suspension which can be easily prepared from the biocidal fine powder and has high biological effect and prolonged stability.

Still a further object of the invention is to provide a suspension of the biocidal fine powder in which no bottom hard caking occurs or precipitation of the biocidal substance.

After an earnest study it was found that it is possible to produce a biocidal fine powder containing at least 50 wt % of particles with diameter of 0.5 micron or less by mixing a dispersion liquid of a biocidal substance with rigid media having particle diameter of 0.5 mm or less and that the thus obtained biocidal fine powder exhibits a notably reinforced biological activity.

The inventors have further found that use of the thus obtained biocidal fine powder as the active agent enables a suspension for agricultural use to be produced which has both a high biological effect and prolonged stability. Because, no bottom hard caking or increased viscosity are caused by natural precipitation of the biocidal substance. Thus this invention has been completed.

This is to say, this invention provides a biocidal fine powder containing at least 50 wt % of particles with diameter of 0.5 micron or below, its manufacturing method and a suspension for agricultural use containing the above powder.

The biocidal fine powder of this invention contains at least 50 wt % of particles with diameter of 0.5 micron or less. It is preferable that the biocidal fine powder of this invention contains at least 50 wt % of particles with diameter of 0.5 micron or less and that the average diameter of the particles in the powder is 0.5 micron or less. It is specially preferable that the powder contains at least 70 wt % of particles with diameter of 0.5 micron or less and that the average diameter of the particles in the powder is 0.4 micron or less.

DETAILED DESCRIPTION OF THE INVENTION AND PREFERRED EMBODIMENTS

The biocidal substance usable in this invention is insoluble in water and includes any biocidal agent which is solid or pasty at room temperature. Any biocidal agent when pulverized according to the method of this invention comes to have an excellent biological effect which could not have been achieved by the conventional method of preparation. It is also possible to prepare the above biocidal substance by combining at least two biocidal agents having different structures.

The following germicides, herbicides, insecticides and miticides or tickicides are listed as water-insoluble biocidal agents which are solid or pasty at ordinary temperature. Germicides: Copper agents; organotin agents; organic arsenical agents; organosulfur agents including sulfur, Dithane (zinc ethylenebis(dithio-carbamate)) and Thiuram (bis(dimethylthiocarbamoyl)-disulfite); organochlorine agents including Daconil (tetrachloroisophthalonitrile) and Rabcide (4,5,6,7-tetrachlorophthalide); Carboxyanhydride type agents, including Oxycarboxin (5,6-dihydro-2-methyl-N-phenyl-1,4-oxatine-3-carboxyamide-4,4-dioxide); Pyrimidine type agents, such as Ethirimol (5-butyl-2-ethylamino-4-hydroxy-6-methylpyridine); Triazole type agents, including Bayleton (1-(4-chlorophenoxy)-3,3-dimethyl-1-(1H-1,2,4,-trizole-1-yl)2-butanone), Cultar ((2RS,3RS)-1-(4-chlorophenyl)-4,4-dimethyl-2-(1H-1,2,4-triazole-1-yl)pentane-3-ol) and Vigil ([1-(2,4-dichlorophenyl)-4,4-dimethyl-2-(1,2,4-triazole-1-yl)pentene-3-ol]); Pyrimidine methanol type agents such as Rubigan ((2-chlorophenyl)-(4-chlorophenyl)-5-pyrimidine methanol); Heterocyclic imido type agents including Sumilex (N-(3,5-dichlorophenyl)-1,2-dimethylchloropropane-1,2-carboxyimide) and Vinclozolin (3-(3,5-dichlorophenyl)-5-ethynyl-5-methyl-2,4-oxazolidinedione) and other agents such as Captan (N-(trichloromethylthio)-4-cyclohexene-1,2-dicarboximide), Difoltan (N-1,1,2,2-tetrachloroethylthio-4-cyclohexene-1,2-dicarboximide), Acricid (2-sec-butyl-4,6-dinitrophenyl 3-methylcrotonate), Topsin M (dimethyl 4,4′-o-phenylene-3,3′-dithiodiallophanate), Benlate (methyl-1-(butylcarbamoyl)-2-benzimidazole carbamate), Aliette (aluminium tri(-O-ethylkisfonate)), Tricylazole (5-methyl-1,2,4-triazole[3,4-b]benzothiazole) and Tachigaren (3-hydroxy-5-methylisoxazole). Herbicides: Diphenylether-system herbicides including NIP (2,4-dichlorophenyl p-nitrophenyl ether) and MO (p-nitrophenyl 2,4,6-trichlorophenyl ether); acid-amide-system herbicides including Stam (3′,4′-dichloropropionanilide) and Dymid (N,N-dimethyl-2,2-diphenylacetamide); carbamate-system herbicides such as Swep (methyl 3,4-dichlorocarbanilate); ureasystem herbicides such as Karmex D (3-(3,4-dichlorophenyl)-1,1-diethylurea); Phenoxypropionic acid type herbicides such as Fenoxaprop-ethyl (ethyl-2-[4-[(6-chloro-2-benzoxazoyl)oxy]phenoxyl]- propionate); Urea type herbicides including Dimefuron (2-tert-butyl-4-(2-chloro-4-(3,3-dimethylureido)-phenyl)1,3,4-oxadiazoline-5-one); Sulfonamide type herbicides including Chlorosulfuron (2-chloro-N[(4-methoxy-6-methyl-1,3,5-triadine-2-yl)aminocarbonyl]-benzensulfoamide) and Sulfometuron Methyl (methyl-2[[[4,6-dimethyl-2-pyrimidyl)amino]carbonyl]amino]-sulfonyl]benzoate); and triazine-system herbicides including Simazine (2-chloro-4,6-bis(ethylamino)-1,3,5-triazine) and Gesaprim (2-chloro-4-ethylamino-6-isopropylamino-1,3,5-triazine). Insecticides: Organic chlorinesystem insecticides such as DDT (1,1,1-trichloro-2,2-bis(p-chlorophenyl)-ethane); organic phosphorus-system insecticides including Kaya-Ace (p-dimethylsulfamyl phenyldiethyl phosphorothionate) and Gardcide (2-chloro-1-(2,4,5-trichlorophenyl)-vinyldimethyl phosphate) that have aromatic rings; carbamate-system insecticides including Denapon (1-naphthyl methylcarbamate), Tsumacide (m-tolyl methylcarbamate), Macbal (3,5-xylyl methylcarbamate), Mipcin (o-cumenyl methylcarbamate) and Suncide (o-isopropoxyphenyl methylcarbamate); Benzoylurea type insecticides, such as Diflubenzuron (1-(4-chlorophenyl)-3-(2,6-difluorobenzoyl)urea) and Trifluoron (2-chloro-N-[[[4-(trifluoromethoxy)phenyl]-amino]carbonyl]benzamide); and other insecticides such as methaldehyde (tetramer of acetaldehyde), Buprofezin (2-tert-butylimino-3-isopropyl-5-phenylperhexylo-1,3,5-thiadiazine-4-one), Ciromazine (N-cyclopropyl-1,3,5-triazine-2,4,6-triamine) and Lannate (S-methyl N-(methylcarbamoyloxy)thioacetimidate). Miticides or Tickicides: Sappiran (p-chlorophenyl p-chlorobenzenesulfonate), Tedion (p-chlorophenyl 2,4,5-trichlorophenyl sulfone), Kelthane (2,2,2-trichloro-1,1-bis(p-chlorophenyl) ethanol), Omite (2-(p-tert-butylphenoxy)cyclohexyl propynyl sulfite), Azocyclotin (1-(tricyclohexylstanyl)-1H-1,2,4-triazole), Fenbutatin-oxide (hexakis(2-methyl-2-phenylpropyl)-distanoxan), and Plictran (tricyclohexyl hydroxy tin).

The biocidal fine powder of this invention is manufactured by mixing a dispersion liquid of a biocidal substance with rigid media having particle diameter of 0.5 mm or less.

A commercially available powder may be used as a biocidal substance in preparing the above dispersion liquid for this invention or a commercially available dispersion liquid may be used. It is preferable that the concentration of the biocidal substance in the dispersion liquid is in the range of 5 to 70 wt % and a high concentration of the biocidal substance is specially preferable in order to achieve high manufacturing efficiency.

It is preferable that the particle diameter of the media used in this invention is 0.5 mm or less preferably in the range of 0.05 to 0.5 mm. The material for the media may be a rigid member such as Ottawa sand, glass, alumina or zircon and is preferable a glass member.

A sand mill, a sand grinder or similar apparatus can be used in pulverizing a mixture containing the biocidal substance and the media. A sand mill or a sand grinder used for this invention may be a generally well known one of either the vertical type or the horizontal type. A disk used for this invention may also be of the usual type.

It is preferable that a temperature of 5° to 30°C. is maintained during the pulverization. A temperature exceeding 30° C. is not favorable because the pulverization can be performed only with difficulty because a long time is needed for the pulverization.

When performing the pulverization, the ratio by volume of the media to the biocidal substance is in the range of 40/60 to 80/20 preferably in the range of 60/40 to 70/30.

The biocidal fine powder according to this invention is obtained by pulverizing the aforementioned mixture by means of a sand mill before the media are separated from the biocidal dispersion liquid by pressure filtration br ultracentrifugation and then washing the media by water as needed.

When performing the above pulverization, the efficiency of the pulverization can be increased by adding a proper dispersing agent to the dispersion liquid of a biocidal substance. The following compounds (1) to (3) are listed as specially favorable dispersing agents. One of these compounds may be used alone or at least two of them may be used in combination.

(1) A water-soluble or water-dispersible polymer containing as essential components at least one compound selected from the monomer group consisting of unsaturated carboxylic acids and their derivatives.

For monomers used in the manufacture of polymer (1), unsaturated monocarboxylic acids such as acrylic acid and methcrylic acid, unsaturated dicarboxylic acids such as maleic acid and the derivatives of the above compounds such as the alkyl esters of the above described acids (such as methyl esters), the alkali metal salts of the above described acids (such as soda salts), the ammonium salts and the organic amine salts (triethanolamine salts) of the above described acids can be used. In addition to these monomers, it is possible to add a copolymerizable monomer such as vinyl acetate, isobutylene, diisobutylene or styrene as a copolymer component.

Polymerization of these monomers is performed according to the conventional well known method. Although there is no restriction to the properties of monomer components and the degree of the polymerization, it is necessary that the polymer is at least water soluble or water dispersible.

An acrylic polymer, a methacrylic polymer, a copolymer consisting of acrylic acid and methacrylic acid, a copolymer consisting of acrylic acid and methyl acrylate, a copolymer consisting of acrylic acid and vinyl acetate, a copolymer consisting of acrylic acid and maleic acid, a copolymer consisting of maleic acid and isobutylene, a copolymer consisting of maleic acid and styrene as well as the alkali metal salts, the ammonia salts and the organic amine salts of the above copolymers are listed as examples. It is possible to use two or more of these polymers.

(2) Polymers of styrene sulfonates

Polymers of styrene sulfonates can be easily manufactured either by polymerizing styrene sulfonates or by sulfonating a polystyrene. They have a skeleton represented by the following formula.

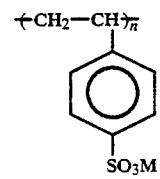

Polymers of styrene sulfonates have a molecular weight of at least 1,000, preferably 10,000 to 3,000,000.

The symbol M in the above formula indicates either the salt of an alkali metal such as Li, Na or K or a compound such as NH₃, an alkylamine or an alkanolamine.

Polymers of styrene sulfonates may be a copolymer consisting of a styrene sulfonate and another monomer. Such a copolymer can be easily manufactured by either copolymerizing a styrene sulfonate and another monomer or by sulfonating a copolymer consisting of styrene and another monomer. The copolymerization may be performed within such a range that the effect of the agricultural agent of this invention is not deteriorated. For the monomer used in the above copolymerization, hydrophobic monomers such as alkyl acrylate, alkyl methacrylate, vinylalkyl ether, vinyl acetate, ethylene, propylene, butylene, butadiene, diisobutylene, vinyl chloride, vinylidene chloride, acrylonitrile and styrene as well as hydrophylic monomers such as acrylic acid, methacrylic acid, maleic acid, fumaric acid, maleic anhydride, vinyl alcohol, acrylamide, methacrylamide, diacetone acrylamide, N-vinylpyrrolidone, 2-acrylamide-2-methylpropane sulfonic acid and methacryl sulfonic acid can be used.

(3) The formalin condensation products (or their salts) of the sulfonation products of polycyclic aromatic compounds which may have a hydrocarbon group as a substituent.

The formalin condensation products of compounds such as petroleum sulfonate derivatives, lignin sulfonate derivatives and naphthalene sulfonate derivatives are tangibly used.

The above compound (3) according to this invention is obtained, for example, by sulfonating naphthalene, an alkyl-substituted naphthalene, anthracene, an alkylsubstituted anthracene, lignin and a compound contained in the petroleum residue and having an aromatic ring by a general method before the sulfonation product is subjected to salt-producing reaction and formalin condensation. Here, it is preferable that the degree of condensation is 1.2 to 30, preferably 1.2 to 10. When the degree of condensation is 1.2 or less, only a small effect is achieved by the condensation. When the degree of condensation exceeds 30, the molecular weight of the resulting compound becomes large and practical problems in solubility and the like arise. Various kinds of polycyclic aromatic compounds can be used. It is preferable that lignin, naphthalene or an alkyl naphthalene containing 1 to 6 carbon atoms is used as the polycyclic aromatic compound used in this invention. It is also possible to use one of the mixtures of these compounds.

An alkali metal such as sodium or potassium, an alkaline earth metal such as calcium as well as an amine and an ammonium salt can be used as salts.

It is preferable that at least 0.1 wt %, preferably 0.5 to 10 wt %, of the above dispersing agents (1) to (3) is added to the dispersion liquid of a biocidal substance in preparing the biocidal fine powder.

The thus obtained biocidal powder contains at least 50 wt % of particles with diameter of 0.5 micron or less. Particle diameters and their distribution were measured by a centrifugal automatic size-distribution-measuring device CAPA-500 manufactured by Horiba Seisakusho (same as in examples). A dispersion liquid containing the biocidal powder has a remarkably improved dispersion stability as compared to the conventional dispersion liquid containing a biocidal substance of large particle diameter. In addition, the dispersion liquid of this invention can be very advantageously used as an agricultural agent because of having a higher biological effect than the conventional dispersion liquid containing a biocidal substance.

Although the suspension of this invention for agricultural use has good dispersion stability, it is possible to add a water-soluble thickener, a dispersing agent, an anti-foaming agent, a decomposition-preventing agent, an aggregation-preventing agent, an adjuvant or a similar agent as needed. The addition of a compound selected from among the following compounds (i) to (ii) as an adjuvant, is specially favorable because a further increased biological effect of the agricultural agent of this invention can be achieved.

(i) Polyoxyalkylene-type nonionic surface active agents

Compounds specified in the following items (1) to (8) are listed as preferable examples.

(1) Products obtained by causing an alkylene oxide to react with a mixture composed of a fatty acid triglyceride and a polyhydric alcohol through addition reaction.

There is no special restriction to the fatty acid triglyceride used in this invention, and the triglycerides of higher fatty acids are generally used. Behenic acid, stearic acid, oleic acid, linolic acid, palmitic acid, myristic acid, lauric acid and caprylic acid can be listed as higher fatty acids. Each of these higher fatty acids may be used alone or at least two of them may be used in combination. The fatty acid triglyceride may be either a natural compound or a synthetic one. Natural fats and oils that are natural fatty acid triglycerides are easily available and suitable for this invention. Animal fats and oils such as beef tallow, lard and mutton tallow and plants' fats and oils such as coconut oil, palm oil, cottonseed oil, castor oil, rapeseed oil, palm-kernal oil, soybean oil, olive oil, linseed oil and corn oil are listed as such natural fats and oils.

For the polyvalent alcohol used in this invention, compounds which contain 2 to 6 hydroxyl groups and 2 to 6 carbon atoms and in which the number of hydroxyl groups does not exceed the number of carbon atoms are preferably used. Ethylene glycol; propylene glycol; glycerol; 1,2-, 1,3- and 2,3-butylene glycol; 1,2-, 1,3-, 2,3- and 2,4-pentylene glycol; 1,2-, 1,3- 2,3-and 2,4-hexylene glycol; butanetriol; pentanetriol; hexanetriol; pentaerythritol; sorbitol; mannitol; xylitol; and dulcitol are listed as such compounds.

Among these polyvalent alcohols, those containing 3 carbon atoms, especially glycerol, are most favorable to achieve the purpose of this invention. It is also possible to use one of the mixtures of the above polyvalent alcohols.

The molar ratio of the fatty acid triglyceride to the polyvalent alcohol used is 1:0.1 to 5 preferably 1:0.2 to 2.

Either one of ethylene oxide, propylene oxide and butylene oxide alone or one of their mixtures may be used as the alkylene oxide added to a mixture composed of a fatty acid triglyceride and a polyvalent alcohol. It is specially preferable to use ethylene oxide alone, propylene oxide alone or a combination of ethylene oxide and propylene oxide. When at least two of the above compounds are jointly used, either random or block copolymers may be produced by the addition reaction.

The molar ratio of the amount of the alkylene oxide to the total amount of the fatty acid triglyceride and the polyvalent alcohol is 1–100:1 preferably 5–60:1.

Conditions for the addition reaction are not specially restricted and the reaction can be performed under the conditions for the reaction generally performed in adding an alkylene oxide to a compound having active hydrogen atoms. Specifically, after a catalytic amount of an alkaline substance is added to a mixture composed of a triglyceride and a polyvalent alcohol in the above described molar ratio, when the mixture is at about 100° to 200° C. the above specified amount of an alkylene oxide is introduced at a pressure of 1 to 5 kg/cm$^2$ in several hours to cause the alkylene oxide to react with the mixture.

The product of this addition reaction is a mixture of various compounds. Although the detailed composition of the mixture has not been clarified, the principal component of the mixture is estimated to be a product that the alkylene oxide added between the fatty acid moiety of the triglyceride and the polyvalent alcohol or glycerol derived from the triglyceride.

(2) Polyoxyalkylene alkyl (or alkenyl) ether

The alkyl (or alkenyl) group should contain 4 to 22 carbon atoms. Either one of oxyethylene, oxypropylene and oxybutylene or one of their mixtures is used as oxyalkylenes. It is most preferable that the proportion of oxyethylene is at least 50 wt % of the total quantity of oxyalkylenes.

The number of moles of oxyalkylenes added is 1 to 100, preferably 3 to 50.

(3) Polyoxyalkylene mono- or di-alkyl (or aryl) phenylether

The alkyl group should contain 4 to 18 carbon atoms. The benzyl group, the phenyl group and the styryl group are listed as aryl groups. Either one of oxyethylene, oxypropylene jand oxybutylene or one of their mixtures is used as oxyalkylenes. It is most preferable that the proportion of oxyethylene is at least 50 wt % of the total quantity of oxyalkylenes.

The number of moles of oxyalkylenes addes is 1 to 100, preferably 3 to 50.

(4) Polyoxyalkylene sorbitan fatty acid ester

The fatty acid should be a higher fatty acid containing 8 to 22 carbon atoms. The degree of esterification is 1 to 4, preferably 1 to 3. Either one of oxyethylene, oxypropylene and oxybutylene or one of their mixtures is used as oxyalkylenes. It is most preferable that the proportion of oxyethylene is at least 50 wt % of the total quantity of oxyalkylenes.

The number of moles of oxyalkylenes added is 1 to 100, preferably 3 to 50.

(5) Polyoxyalkylene sorbitol fatty acid ester

The fatty acid should be a higher fatty acid containing 8 to 22 carbon atoms. The degree of esterification is 1 to 6 preferably, 3 to 5. Either one of oxyethylene, oxypropylene and oxybutylene or one of their mixtures is used as oxyalkylenes. It is most preferable that the proportion of oxyethylene is at least 50 wt % of the total quantity of oxyalkylenes.

The number of moles of oxyalkylenes added is 1 to 100, preferably 3 to 50.

(6) Polyoxyalkylene sorbitol alkylether

The alkyl group should contain 8 to 22 carbon atoms. The degree of esterification is 1 to 6, preferably 3 to 5. Either one of oxyethylene, oxypropylene and oxybutylene or one of their mixtures is used as oxyalkylenes. It is most preferable that the proportion of oxyethylene is at least 50 wt % of the total quantity of oxyalkylenes.

The number of moles of oxyalkylenes added is 1 to 100, preferably 3 to 50.

(7) Polyoxyalkylene alkyl (or alkenyl) amine

The alkyl (or alkenyl) group contains 4 to 22 carbon atoms. Either one of oxyethylene, oxypropylene and oxybutylene or one of their mixtures is used as oxyalkylenes. It is most preferable that the proportion of oxyethylene is at least 50 wt % of the total quantity of oxyalkylenes.

(8) Polyoxyethylene/polyoxypropylene block polymer

It is preferable that the block polymer has a molecular weight of 1,000 to 10,000.

It is possible to use at least two of compounds (1) to (8) in combination.

(ii) Polyoxyalkylene alkyl (or alkylaryl) ether phosphoric ester or its salt

There is no special restriction to the method of preparing this compound and it is manufactured by a generally well known method. For example, the compound is prepared by adding an alkylene oxide to an alcohol or an alkyl phenol before the addition product is caused to react with phosphorus pentoxide, then neutralizing the reaction product as needed.

The alcohol used as the starting material has either a straight-chain or branched-chain alkyl group containing 1 to 2 carbon atoms or an alkenyl group or a hydroxyalkyl group containing double bonds or hydroxyl groups in the chain. It is preferable that the alcohol contains 4 to 18 carbon atoms, contains 0 to 4 preferably 0 to 2 double bonds and contains 0 to 4 preferably 0 to 2 hydroxyl groups. Compounds such as butanol, 2-ethyl hexanol, lauryl alcohol, stearyl alcohol and oleyl alcohol are listed as alcohols used for this invention. It is preferable that the above alkyl phenol has an alkyl group containing 4 to 18 carbon atoms. Ethylene oxide, propylene oxide and butylene oxide are listed as alkylene oxides which can be added to the alcohol to form a polyoxyalkylene chain. Each of these compounds may be used alone or at least two of them may be subjected to the addition of block or random polymers. The number of moles of alkylene oxides added is 1 to 100, preferably 1 to 50.

The above addition reaction can be performed by a well-known method, for example, by introducing an alkylene oxide at 50° to 200° C. in a pressure of 1 to 5 kg/cm$^2$ under the presence of an acid or alkali catalyst so as to cause the alkylene oxide to react with the mixture. There are several methods for phosphorylating a polyoxyalkylene alkyl (or alkylphenol) ether. For example, a phosphoric ester can be easily prepared by mixing 3 moles of a polyoxyalkylene alkyl ether with 1 mole of phosphorus pentoxide and subjecting the mixture to reaction at 80° to 100° C. for about 6 hours. The thus obtained polyoxyalkylene alkyl (or alkylphenol) ether phosphoric ester is a mixture composed of equal amounts of a monoester and a diester. Both of a monoester or a diester exhibit a superior effect as an adjuvant for this invention. Especially, a monoester such as polyoxyalkylene alkyl ether phosphoric monoester or its salt exhibits a superior effect.

Furthermore, a polyoxyalkylene alkyl ether phosphoric ester salt is obtained by neutralizing the above phosphoric ester by means of a base. The thus obtained phosphoric ester salt also has a superior effect of increasing the biological effect of the agricultural agent of this invention. For the above salt, alkali metal salts, alkaline earth metal salts, monoethanolamine salts, diethanolamine salts, triethanolamine salts and ammonium salts are listed.

In this invention, the ratio by weight of the biocidal powder to a compound selected from groups (i) or (ii) is at least 1:0.05 to 20, and is preferably 1:0.2 to 20 and more preferably 1:0.5 to 15.

In addition to polymer compounds already described in the granulation method, a non-ionic surface active agent or/and an anionic surface active agent can be used as dispersion agent(s) added in preparing the aforementioned agricultural agent of this invention. For the above non-ionic surface active agent, polyoxyethylene (hereafter abbreviated as POE) alkyl (containing 6 to 22 carbon atoms) ether, POE alkyl (containing 4 to 18 carbon atoms) phenolether, polyoxypropylene polyoxyethylene (block or random) alkylether, POE phenylphenol ether, POE styrenated phenolether and POE tribenzyl phenolether are listed. For the above anionic surface active agent, lignin sulfonate, alkylbenzene sulfonate, alkylsulfonate, POE alkyl sulfonate, POE alkyl phenylether sulfonate, POE alkyl phenylether phosphoric ester salt, POE phenyl phenolether sulfonate, POE phenyl phenolether phosphoric ester, naphthalene sulfonate, naphthalenesulfonic acid formalin condensate, POE tribenzyl phenolether sulfonate and POE tribenzylphenyl phenolether phosphoric ester salt are listed. One of these compounds may be used alone or one of their mixtures may be used. The concentration of the above surface active agents in the agricultural agent is 0 to 20 wt%, preferably 1 to 10 wt %.

For a water-soluble thickener, any of natural, semi-synthetic and synthetic thickeners can be used. Xanthan Gum and Zanflo derived from microorganisms as well as pectin, gum arabic and Guar rubber derived from plants are listed as natural thickeners. The methylation products, carboxyalkylation products and hydroxyalkylation products (including methylcellulose, carboxymethylcellulose and hydroxymethylcellulose) of cellulose or starch derivatives are listed as semisynthetic thickeners. Polyacrylates, polymaleinates and polyvinyl pyrrolidone are listed as synthetic thickeners. The concentration of the water-soluble thickener in the agricultural agent is about 0 to 3.0 wt %, preferably about 0.05 to 0.5 wt %.

It is preferable, in some cases, that up to about 2 wt % of an anti-foaming agent is added in manufacturing the agricultural agent in order to prevent any foaming of the agent during its manufacturing. It is also preferable that up to about 7 wt % of a decomposition-preventing agent is contained especially in an organic phosphorus-system biocidal agent in order to prevent its decomposition during its storage. There is no special restriction to the anti-foaming agent used in this invention, and propylene glycol and silicone oil are listed as anti-foaming agents. For the decomposition-preventing agent used in this invention, epichlorohydrin, phenylglycidyl ether and allylglycidyl ether are listed. In addition to these agents, it is possible to add an agglutination-preventing agent for a solid biocidal agent (such as polyoxyethylenepolyoxypropylene block polymer) as well as a drift preventing agent (such as sorbitol) as desired.

An example of the agricultural agent of this invention is as follows:

| | | |
|---|---|---|
| (A) Biocidal fine powder | 10 to 60 | wt % |
| (B) One selected from compounds listed in (i) to (ii) | 10 to 60 | " |
| (C) Dispersing agent | 0 to 20 | " |
| (D) Water-soluble thickener | 0 to 3 | " |
| (E) Anti-foaming agent | 0 to 2 | " |
| (F) Decomposition-preventing agent | 0 to 7 | " |
| (G) Water | 10 to 80 | " |

When preparing the agricultural agent of this invention, there is no special restriction to the order of adding the components.

The mechanism of the reinforced biological effect of the biocidal fine powder according to this invention has not been clarified. The notably increased biological activity of the biocidal fine powder is considered to be due to the phenomenon that minute particles of the powder can easily intrude through air holes existing on the surfaces of leaves as well as through small cracks of the cuticular layer.

Furthermore, since the suspension of this invention for agricultural use contains as an adjuvant a compound selected from groups specified in (i) to (ii) which has a very strong ability of solubilizing the biocidal agent, it is estimated that the particle diameter of the biocidal fine powder is further decreased by the use of the above adjuvant and the biocidal fine powder with further decreased particle diameter can more promptly permeate through the surfaces of plants as well into insect bodies and microbe cells.

Owing to the advent of this invention, it became possible to manufacture a biocidal fine powder containing at least 50 wt % of particles with diameter of 0.5 micron or less. The thus obtained biocidal fine powder has a higher biological effect compared to the conventional biocidal powder of large particle diameter. Thus, a suspension for agricultural use containing the biocidal fine powder of this invention has good dispersion stability and an excellent biological effect.

Other features of the invention will become apparent in the course of the following descriptions of exemplary embodiments which are given for illustration of the invention and are not intended to be limiting thereof.

EXAMPLES

EXAMPLE 1

60 g of Topsin M powder, 4 g of a dispersing agent represented by formula $$\pm CH_2-CH\pm_n$$
$$\quad\quad | $$
$$\quad COO^-Na^+$$

(molecular weight: about 350,000), 55 g of water and 140 g of glass beads (media) of 0.1 to 0.2 mm diameter are mixed (the ratio by volume of the media to the dispersion liquid=50/50), and the mixture is put in a sand grinder of 400 ml capacity (manufactured by Igarashi Kikai) in which a disk is rotated at a peripheral speed of 6 m/second for 12 hours. The temperature of the internal atmosphere of the sand grinder is maintained at 20° to 25° C. After the pulverization is completed, the mixture is subjected to pressure filtration thereby obtaining about 100 g of a pulverized Topsin M dispersion liquid. It is possible to recover about 97 wt % of the Topsin M by washing the separated media with 70 g of water twice.

As shown in Table 1, 72 wt % of the particles in the pulverized Topsin M have a particle diameter of 0.5 micron or less.

TABLE 1

| Dispersion of Topsin M | Size Distribution (wt %) |
| --- | --- |
| 1.0μ or more | 0 |
| 1.0–0.8 | 10 |
| 0.8–0.5 | 20 |
| 0.5–0.2 | 44 |
| 0.2 or less | 28 |

EXAMPLE 2

46 g of Rabcide (germicide) powder, 4.5 g of a water-soluble copolymer salt represented by formula

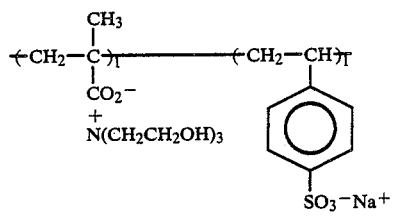

(molecular weight: 680,000), 63 g of water and 187 g of glass beads (media) of 0.1 to 0.2 mm diameter are mixed (the ratio by volume of the media to the dispersion liquid=63/37), and the mixture is put in a sand grinder of 400 ml capacity (manufactured by Igarashi Kikai) in which a disk is rotated at a peripheral speed of 6 m/second for 12 hours. The temperature of the internal atmosphere of the sand grinder is maintained at 20° to 25° C. After that, the mixture is subjected to pressure filtration thereby obtaining 60 g of a pulverized Rabcide dispersion liquid. It is possible to recover 98 wt % of the Rabcide by washing the separated media with 70 g of water twice.

As shown in Table 2, 100 wt % of the particles in the pulverized Rabcide have a particle diameter of 0.5 micron or less.

EXAMPLE 3

56 g of Simazine (herbicide), 4.5 g of a water-soluble copolymer salt represented by formula

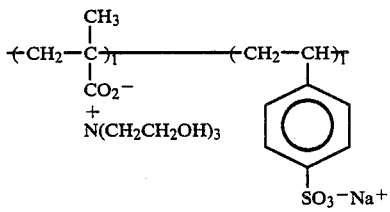

(molecular weight: 320,000), 39.5 g of water and 187 g of glass beads (media) of 0.1 to 0.2 mm diameter are mixed (the ratio by volume of the media to the dispersion liquid=53/47), and the mixture is put in a sand grinder of 400 ml capacity (manufactured by Igarashi Kikai) in which a disk is rotated at a peripheral speed of 6 m/second for 12 hours. The temperature of the internal atmosphere of the sand grinder is maintained at 20° to 25° C. After that, the mixture is subjected to pressure filtration thereby obtaining 60 g of a pulverized Simazine dispersion liquid.

As shown in Table 2, 88 wt % of the particle in the pulverized Simazine have a particle diameter of 0.5 micron or less.

EXAMPLE 4

45.5 g of Karmex D (herbicide), 4.5 g of the Na salt of naphthalenesulfonic acid formalin condensate (condensation degree: 4), 50 g of water and 180 g of glass beads (media) of 0.1 to 0.2 mm diameter are mixed (the ratio by volume of the media to the dispersion liquid=50/50), and the mixture is put in a sand grinder of 400 ml capacity (manufactured by Igarashi Kikai) in which a disk is rotated at a peripheral speed of 6 m/second for 3 hours. The temperature of the internal atmosphere of the sand grinder is maintained at 20° to 25° C. After that, the mixture is subjected to pressure filtration thereby obtaining 68 g of a pulverized Karmex D.

As shown in Table 2, 95 wt % of the particles in the pulverized Karmex D have a particle diameter of 0.5 micron or less.

TABLE 2

| Dispersion | Process Time (hr.) | Example 2 | | | Example 3 | | Example 4 |
| --- | --- | --- | --- | --- | --- | --- | --- |
| | | 3 | 5 | 12 | 6 | 12 | 3 |
| Size Distribution (wt %) | | | | | | | |
| 0.5μ or more | | 5 | 0 | 0 | 41 | 12 | 5 |
| 0.5–0.2 | | 72 | 5 | 4 | 50 | 79 | 84 |
| 0.2–0.1 | | 18 | 69 | 69 | 5 | 5 | 10 |
| 0.1–0.05 | | 5 | 21 | 22 | 4 | 4 | 1 |
| 0.05 or less | | 0 | 5 | 5 | 0 | 0 | 0 |

EXAMPLE 5

45.5 g of Tsumacide (insecticide) powder, 4.5 g of a water-soluble copolymer salt represented by formula

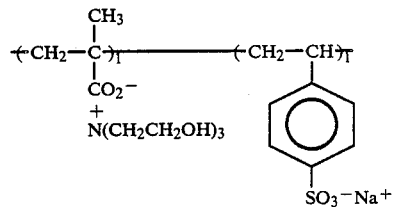

(molecular weight: 260,000), 50 g of water and 187 g of glass beads (media) of 0.1 to 0.2 mm diameter are mixed (the ratio by volume of the media to the dispersion liquid=50/50), and the mixture is put in a sand grinder of 400 ml capacity (manufactured by Igarashi Kikai) in which a disk is rotated at a peripheral speed of 6 m/second for 8 hours. The temperature of the internal atmosphere of the sand grinder is maintained at 20° to 25° C. After that, the mixture is subjected to pressure filtration thereby obtaining 70 g of a pulverized Tsumacide dispersion liquid.

As shown in Table 3, 90 wt % of the particles in the pulverized Tsumacide have a particle diameter of 0.5 micron or less.

EXAMPLE 6

45.5 g of Lannate (insecticide), 4.5 g of a water-soluble copolymer salt represented by formula

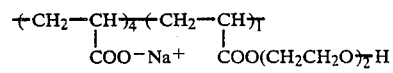

(molecular weight: 220,000), 50 g of water and 187 g of glass beads (media) of 0.1 to 0.2 mm diameter are mixed (the ratio by volume of the media to the dispersion liquid=50/50), and the mixture is put in a sand grinder of 400 ml capacity (manufactured by Igarashi Kikai) in which a disk is rotated at a peripheral speed of 6 m/second for 8 hours. The temperature of the internal atmosphere of the sand grinder is maintained at 20° to 25° C. After that, the mixture is subjected to pressure filtration thereby obtaining 45 g of a pulverized Lannate dispersion liquid.

As shown in Table 3, 74 wt % of the particles in the pulverized Lannate have a particle diameter of 0.5 micron or less.

EXAMPLE 7

45.5 g of Plictran (miticide) powder, 4.5 g of a water-soluble copolymer salt represented by formula $$+CH_3-\underset{\underset{COO^-Na^+}{|}}{\overset{\overset{CH_3}{|}}{C}}\!\!\!\rightarrow_{\!\!\overline{n}}\!\!+CH_2-\underset{\underset{CH_3}{|}}{\overset{\overset{CH_3}{|}}{C}}\!\!\!\rightarrow_{\!\!\overline{n}}$$

(molecular weight: 180,000), 50 g of water and 187 g of glass beads (media) of 0.1 to 0.2 mm diameter are mixed (the ratio by volume of the media to the dispersion liquid=50/50), and the mixture is put in a sand grinder (manufactured by Igarashi Kikai) in which a disk is rotated at a peripheral speed of 6 m/second for 8 hours. The temperature of the internal atmosphere of the sand grinder is maintained at 20° to 25° C. After that, the mixture is subjected to pressure filtration thereby obtaining 70 g of a pulverized Plictran dispersion liquid.

As shown in Table 3, 100 wt % of the particles in the pulverized Plictran have a particle diameter of 0.5 micron or less.

TABLE 3

| Dispersion | Example 5 | Example 6 | Example 7 |
|---|---|---|---|
| Size Distribution (wt %) | | | |
| 0.5μ or more | 10 | 26 | 0 |
| 0.5–0.2 | 72 | 64 | 84 |
| 0.2–0.1 | 12 | 5 | 10 |
| 0.1–0.05 | 6 | 5 | 6 |
| 0.05 or less | 0 | 0 | 0 |

EXAMPLE 8

The Topsin M dispersion liquid obtained in Example 1 (according to this invention) and Topsin M dispersion liquids (conventional products) having particle diameter distributions shown in Table 4 were used to carry out a biological experiment according to the following method. The result of the experiment are shown in Table 5.

TABLE 4

| Dispersion of Topsin M (Prior Art) | Size Distribution (wt %) |
|---|---|
| 1.0μ or more | 65 |
| 1.0–0.8 | 20 |
| 0.8–0.5 | 10 |
| 0.5–0.2 | 5 |
| 0.2 or less | 0 |

(Method of the Experiment)

Mandarin oranges were immersed in a suspension liquid of gray mold spores for six hours. Following that, various concentrations of each of the Topsin M dispersion liquid of this invention and the conventional Topsin M dispersion liquids were sprayed on the treated mandarin oranges (1 ml/mandarin orange). The thus treated mandarin oranges were then stored at 27° C. for two weeks to investigate the control effects of these dispersion liquids. Evaluation of the control effect was performed in accordance with the following evaluation criteria.

| Fruit Infection | Evaluation |
|---|---|
| Healthy Fruit | 5 |
| 20% Infection | 4 |
| 50% " | 3 |
| 80% " | 2 |
| 100% " | 1 |

TABLE 5

| Concentration of Topsin M | Example 1 (Inventive Product) | Prior Art |
|---|---|---|
| 160 ppm | 5 | 5 |
| 80 | 5 | 4 |
| 40 | 5 | 3 |
| 20 | 5 | 2 |
| 10 | 4 | 1 |
| 5 | 3 | 1 |
| Non-treatment | 1 | 1 |

EXAMPLE 9

The Rabcide dispersion liquid obtained in Example 2 (according to this invention) and the 20% Rabcide flowable (conventional product) were used to carry out a biological experiment according to the following method. The results of the experiment are shown in Table 6.

(Method of the Experiment)

Six hours after a suspension liquid of rice blast spores was sprayed on 4-leaf stage rice plants (Nihonbare) of 13 cm height, various concentrations of each of the Rabcide dispersion liquid of this invention and the conventional 20% Rabcide flowable were sprayed on the treated rice plants. The thus treated rice plants were then left at 27° C. at a relative humidity of 90% for two weeks. After that, the number of lesions observed in the treated division and that of lesions observed in the non-treated division were counted in order to obtain a control percentage.

TABLE 6

| Concentration of Rabcide | Example 2 (Inventive Product) | 20% Flowable (Prior Art) |
|---|---|---|
| 100 | 100% | 100% |
| 50 | 100 | 64 |
| 25 | 100 | 50 |
| 12.5 | 90 | 30 |
| 6.25 | 85 | 20 |

EXAMPLE 10

The herbicide dispersion liquids obtained in Examples 3 and 4 (according to this invention) as well as 50% Simazine water-dispersible powder and 50% Karmex D 50 water-dispersible powder (that are commercial products corresponding to the above dispersion liquids)

were used to carry out a biological experiment according to the following method. The results are shown in Table 7.

(Method of the Experiment)

After crab grasses were grown until they became 3 to 4 leaf stages of 7 cm height, each of the dispersion liquids of this invention and the commercial products was sprayed on the grown grasses in order to investigate the herbicidal effects of these agents. Evaluation of the herbicidal effect was performed by measuring the raw height of the portions exposed above the ground of the grasses of the treated division and that of the non-treated division in order to obtain a herbicidal percentage. The amount of each aqueous dilute liquid sprayed was adjusted to 200 /are.

TABLE 7

| Amount of Herbicide | Example 3 (Inventive Product) | 50% Simazine Water-Dispersible Powder (Commercial Product) | Example 4 (Inventive Product) | 50% Karmex D50 Water-Dispersible Powder (Commercial Product) |
|---|---|---|---|---|
| 50 g/are | 100% | 65% | 100% | 70% |
| 40 " | 90 | 45 | 100 | 55 |
| 30 " | 75 | 30 | 89 | 35 |
| 20 " | 70 | 25 | 80 | 20 |
| 10 " | 40 | 0 | 65 | 0 |

Example 11

The insecticide dispersion liquids obtained in Examples 5 and 6 (according to this invention) and 30% Tsumacide emulsion and 45% Lannate water-dispersible powder (that are commercial products corresponding to the above dispersion liquids) were used to carry out a biologial experiment according to the following method. The results of the experiment are shown in Table 8.

(Method of the Experiment)

After rice plants (Nihonbare) were grown until they became 7-leaf stage of 25 cm height, various concentrations of each of the dispersion liquids of this invention and the commercial products were sprayed on the grown rice plants (10 ml/plant). Six hours after the spraying, 50 green rice leafhoppers were released in each division. Seven days after green rice leafhoppers were released, the ratio of the number of insects killed in the treated division to that killed in the non treated division was obtained as an insecticidal rate.

TABLE 8

| Concentration of Active Ingredient | Example 5 (Inventive Product) | Emulsion of 30% Tsumacide (Commercial Product) | Example 6 (Inventive Product) | 45% Lannate Water-Dispersible Powder (Commercial Product) |
|---|---|---|---|---|
| 50 ppm | 100 | 100 | 100 | 100 |
| 25 | 85 | 78 | 95 | 82 |
| 12.5 | 75 | 52 | 90 | 65 |
| 6.25 | 50 | 32 | 65 | 40 |

EXAMPLE 12

The Plictran dispersion liquid obtained in Example 7 (according to this invention) and 50% Plictran water-dispersible powder (commercial) were used to carry out a biological experiment according to the following method. The results of the experiment are shown in Table 9.

(Method of the Experiment)

Thirty female adults of two-spotted mites were implanted in each hericot leaf disk of 5 cm×5 cm before they were left at 25° C. for one day. Following that, various concentrations of each of the dispersion liquids of this invention and the commercial product (0.3 ml/disk) were repeatedly sprayed 10 times. Three days after the spraying, the ratio of the number of mites killed in the treated division to that of mites killed in the non-treated division was obtained as a miticidal rate.

TABLE 9

| Concentration of Prictran | Example 7 (Inventive Product) | 50% Plictran Water-Dispersible Powder (Commercial Product) |
|---|---|---|
| 500 ppm | 100% | 100% |
| 250 | 100 | 90 |
| 125 | 100 | 74 |
| 62.5 | 90 | 50 |
| 31.75 | 85 | 35 |

EXAMPLE 13

This experiment was conducted in order to investigate the activities of various kinds of adjuvants reinforcing the biological effect of the pulverized Topsin M sol indicated in Example 1. Chinese cabbages were inoculated with bacteria of soft rot, then the pulverized Topsin M sol and various concentrations of an adjuvant were sprayed after the disease was produced in the inoculated cabbages (7 days after the inoculation). The thus treated Chinese cabbages were then left at high temperature under a condition of high humidity for 7 days. Following that, the diameter of each lesion after the production of the disease as well as that after the treatment with the agents were measured in order to evaluate the curing effect by obtaining prevention rate according to the formula specified below. After the disease was produced in the treated Chinese cabbages, those having lesions of 10 mm diameter were used. The results are shown in Table 10.

$$\text{Prevention rate:} \frac{\text{Diameter of lesion after production of disease} - \text{Diameter of lesion after treatment with agents}}{\text{Diameter of lesion after production of disease}} \times 100$$

TABLE 10

| Concentration of Sols Having Fine Particles and Commercial Products | Suspension of Agricultural Chemicals | | Diameter of Affected Portions after Treatment of the Chemicals (mm) | Prevention Rate (%) |
|---|---|---|---|---|
| | Adjuvant and its Concentration (ppm) | | | |
| Sol Having Fine Particles of Topsin M (Example 1) | | | | |
| 200 ppm | Soy bean oil/ Glycerine (1/1) $(EO)_5(PO)_{10}$ | 500 | 0 | 100 |
| | | 250 | 0 | 100 |
| | | 125 | 0 | 100 |
| | | 62.5 | 0 | 100 |
| 100 ppm | " | 500 | 0 | 100 |
| | | 250 | 0 | 100 |
| | | 125 | 0 | 100 |
| | | 62.5 | 1 | 90 |
| | | 0 | 2 | 80 |
| 50 ppm | " | 500 | 0 | 100 |
| | | 250 | 0 | 100 |
| | | 125 | 0 | 100 |
| | | 62.5 | 1 | 90 |
| | | 0 | 3 | 70 |
| Topsin M Water-Dispersible Powder (Commercial Product) | | | | |
| 500 ppm | — | | 2 | 80 |
| 200 ppm | — | | 5 | 50 |
| 100 ppm | — | | 10 | 0 |
| 50 ppm | — | | 10 | 0 |
| Non-treatment | — | | 29 | — |

Example 14

Six hours after rice plants of 5-leaf stage were treated with an aqueous suspension containing the pulverized Rabcide sol indicated in Example 2, a suspension liquid of rice blast spores was sprayed. The thus treated rice plants were then left at high temperature under a condition of high humidity for 10 days. Following that, the number of rice blast lesions for each division was counted in order to calculate prevention rate according to the formula specified below. The results are shown in Table 11.

$$\text{Prevention rate:} \left(1 - \frac{\text{Number of lesions in treated division}}{\text{Number of lesions in non-treated division}}\right) \times 100$$

TABLE 11

| Concentration of Rabcide Having Fine Particles and Commercially Sold Labcide | Suspension of Agricultural Chemicals | | Number of Affected Portions (per 1 rice plant) | Prevention Rate (%) |
|---|---|---|---|---|
| | Adjuvant and its Concentration (ppm) | | | |
| Sol Having Fine Particles of Rabcide (Example 2) | | | | |
| 500 ppm | Soy bean oil/ $(EO)_{25}$/ Glycerine | 500 | 0 | 100 |
| | | 250 | 0 | 100 |
| | | 125 | 0 | 100 |
| | | 62.5 | 0 | 100 |
| | | 0 | 3 | 96 |
| | Polyoxyethylene (EOP=60) sorbitol oleate | 500 | 0 | 100 |
| | | 250 | 0 | 100 |
| | | 125 | 0 | 100 |
| | | 62.5 | 1 | 98 |
| | | 0 | 3 | 96 |
| | Polyoxyethylene (EOP=15) laurylether phosphate | 500 | 0 | 100 |
| | | 250 | 0 | 100 |
| | | 125 | 0 | 100 |
| | | 62.5 | 0 | 100 |
| | | 0 | 3 | 96 |
| Rabcide Water-Dispersible Powder (Commercial Product) | | | | |
| 250 ppm | — | | 5 | 94 |

TABLE 11-continued

| Suspension of Agricultural Chemicals | | | |
|---|---|---|---|
| Concentration of Rabcide Having Fine Particles and Commercially Sold Labcide | Adjuvant and its Concentration (ppm) | Number of Affected Portions (per 1 rice plant) | Prevention Rate (%) |
| 100 ppm | — | 11 | 87 |
| 50 ppm | — | 24 | 71 |
| Non-treatment | — | 84 | — |

EXAMPLE 15

This experiment was conducted in order to investigate the activities of various kinds of adjuvants reinforcing the biological effect of the pulverized Simazine sol and the pulverized Karmex D sol indicated in Examples 3 and 4. After 20 crab grasses per pot were grown until they became 5 to 6 leaf stage of 12 cm height, the pulverized Simazine or Karmex D sol and various concentrations of an adjuvant were sprayed. The thus treated crab grasses were then left in a hothouse for 14 days. Following that, the raw weight of the portions exposed above the ground of the grasses of the treated division and that of the non-treated division were measured in order to obtain a herbicidal percentage. The results are shown in Table 12.

TABLE 12

| | Suspension of Agricultural Chemicals | | |
|---|---|---|---|
| Amount and Concentration of Sols Having Fine Particles and Commercial Products | Adjuvant and its Concentration (ppm) | Amount in Living-body (g) | Killing Rate of Herb (%) |
| Sol Having Fine Particles of Simazine (Example 3) 2500 ppm | | | |
| Valid Cont. | Polyoxyethylene (EOP$_{10}$) lauryl ether | 1000 0 | 100 |
| 50 g/are | Polyoxyethylene (EOP$_{20}$) oleate | " 0 | 100 |
| | Polyoxyethylene (EOP$_{15}$) sorbitan stearate | " 0 | 100 |
| | Polyoxyethylene (EOP$_{30}$)oleylamine | " 6 | 95 |
| | Polyoxyethylene(10)polyoxypropylene (80) block polymer | " 19.2 | 84 |
| Valid Cont. | Same as above | " 0 | 100 |
| 25 g/are | | " 0 | 100 |
| | | " 12 | 90 |
| | | " 30 | 75 |
| | | " 36 | 70 |
| Sol Having Fine Particles of Karmex (Example 4) 2500 ppm | | | |
| Valid Cont. | Soy bean oil/Glycerine (1/1) | | |
| 50 g/are | (EO)$_{10}$(PO)$_2$ | " 0 | 100 |
| | Polyoxyethylene(20)nonylphenyl ether | " 0 | 100 |
| | Polyoxyethylene(30)dinonylphenyl ether | " 0 | 100 |
| | Polyoxyethynene(30)nonylphenyl ether phosphate | " 0 | 100 |
| Valid Cont. | Same as above | " 12 | 90 |
| 25 g/are | | " 18 | 85 |
| | | " 24 | 80 |
| | | " 15.6 | 87 |
| Simazine Water-Dispersible Powder (Commercial Product) 2500 ppm | | | |
| Valid Cont. 50 g/are | | — 62.4 | 48 |
| Valid Cont. 25 g/are | | — 97.2 | 19 |
| 50% Karmex D50 Water-Dispersible Powder (Commercial Product) 2500 ppm | | | |
| Valid Cont. 50 g/are | | — 43.2 | 64 |
| Valid Cont. 25 g/are | | — 84 | 30 |
| Non-treatment | | — 120 | — |

EXAMPLE 16

This experiment was conducted in order to investigate the activities of various kinds of adjuvants reinforcing the biological effect of the pulverized Tsumacide sol indicated in Example 5. The pulverized Tsumacide sol and various concentrations of an adjuvant were sprayed on rice plants of 7 to 6 leaf stage. One day after the spraying, 30 adults of green rice leafhoppers were released in each division. Then an insecticidal rate for each treated division was obtained 7 days after. The results are shown in Table 13.

TABLE 13

| Suspension of Agricultural Chemicals | | | |
|---|---|---|---|
| Concentration of Sols having Fine Particles and Commercial Products | Adjuvant and its Concentration (ppm) | | Killing Rate of Insects (%) |
| Sol Having Fine Particles of Tsumacide (Example 5) | | | |
| 100 ppm | Polyoxyethylene (20) polyoxypropylene (5) oleate | 1000 500 250 100 0 | 100 100 90 85 65 |
| 50 ppm | Same as above | 1000 500 250 100 0 | 100 100 75 60 50 |
| 100 ppm | Polyoxyethylene (20) polyoxypropylene (5) sorbitan monolaurate | 1000 500 250 100 0 | 100 100 80 70 65 |
| 50 ppm | Same as above | 1000 500 250 100 0 | 100 100 70 60 50 |
| Emulsion of 40% Tsumacide (Commercial Product) | | | |
| 100 ppm | — | | 50 |
| 50 ppm | — | | 20 |

EXAMPLE 17

This experiment was conducted in order to investigate the activities of various kinds of adjuvants reinforcing the biological effect of the pulverized Lannate sol indicated in Example 6. Each of various concentrations of suspensions prepared by diluting the product were sprayed on 20 larvae of cutworms and in insecticidal rate for each treated division was obtained 7 days after the spraying. The results are shown in Table 14.

TABLE 14

| Suspension of Agricultural Chemicals | | | |
|---|---|---|---|
| Concentration of Sols having Fine Particles and Commercial Products | Adjuvant and its Concentration (ppm) | | Killing Rate of Insects (%) |
| Sol Having Fine Particles of Lannate (Example 6) | | | |
| 500 ppm | Diethanolamine salt of polyoxyethylene (25) polyoxypropylene (5) oleyl ether phosphate | 5000 2500 1000 500 100 0 | 100 100 100 85 80 75 |
| 250 ppm | Same as above | 5000 2500 1000 500 100 0 | 100 100 90 80 75 50 |

TABLE 14-continued

| Suspension of Agricultural Chemicals | | | |
|---|---|---|---|
| Concentration of Sols having Fine Particles and Commercial Products | Adjuvant and its Concentration (ppm) | | Killing Rate of Insects (%) |
| Lannate Water-Dispersible Powder (Commercial Product) | | | |
| 500 ppm | — | | 45 |
| 250 ppm | — | | 25 |

EXAMPLE 18

This experiment was conducted in order to investigate the activities of various kinds of adjuvants reinforcing the biological effect of the pulverized Plictran sol indicated in Example 7. Various concentrations of the pulverized Plictran sol and various concentrations of adjuvants were sprayed on soybeans of 10 to 11 leaf stage. One day after the treatment, 20 female adults of two-spotted mites were implanted in the treated soybeans. Three days after the implantation, the total number of mites in each division was counted in order to calculate a miticidal rate according to the formula specified below.

$$\text{Miticidal rate:} \left(1 - \frac{\text{Total number of mites in treated division}}{\text{Total number of mites in non-treated division}}\right) \times 100$$

TABLE 15

| Suspension of Agricultural Chemicals | | | | |
|---|---|---|---|---|
| Concentration of Sols having Fine Particles and Commercial Products | Adjuvant and its Concentration (ppm) | | Count of Mites | Killing Rate of Insects (%) |
| Sol Having Fine Particles of Tsumacide (Example 5) | | | | |
| 200 ppm | Soy bean oil/ Glycerine (1/1) (EO)$_{50}$(PO)$_5$ | 500 250 0 | 0 0 0 | 100 100 100 |
| 100 ppm | Same as above | 500 250 0 | 0 15 54 | 100 98 92 |
| 50 ppm | Same as above | 500 250 0 | 10 44 75 | 98 94 89 |
| Plictran Water-Dispersible Powder (Commercial Product) | | | | |
| 200 ppm | — | | 25 | 96 |
| 100 ppm | — | | 110 | 84 |
| 50 ppm | — | | 205 | 70 |
| Non-treatment | — | | 685 | — |

EXAMPLE 19

50 g of Diflubenzuron powder (insecticide), 3 g of a dispersing agent represented by the formula

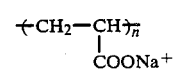

(molecular weight: about 300,000), 60 g of water and 120 g of glass beads (media) of 0.1 to 0.2 mm diameter are mixed (the ratio by volume of the media to the dispersion liquid=50/50), and the mixture is put in a sand grinder of 400 ml capacity (manufactured by Igarashi Kikai) in which a disk rotated at a peripheral speed of 5 m/second for 12 hours. The temperature of the internal atmosphere of the sand grinder is maintained at 20° to 25° C. After the pulverization is completed, the mixture is subjected to pressure filtration thereby obtaining about 100 g of a pulverized Diflubenzuron dispersion liquid. It is possible to recover about 95 wt % of the Diflubenzuron by washing the separated media with 60 g of water twice.

As shown in Table 16, 80 wt % of the particles in the pulverized Diflubenzuron have a particle diameter of 0.5 micron or less.

TABLE 16

| Dispersion of Diflubenzuron | Size Distribution (wt %) |
|---|---|
| 1.0 micron or more | 0 |
| 1.0–0.8 | 5 |
| 0.8–0.5 | 15 |
| 0.5–0.2 | 38 |
| 0.2 micron or less | 42 |

EXAMPLE 20

60 g of Trifluron powder (insecticide), 3 g of a dispersing agent represented by the formula

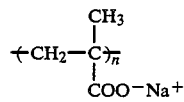

(molecular weight: about 200,000), 50 g of water and 120 g of glass beads (media) of 0.1 to 0.2 mm diameter are mixed (the ratio by volume of the media to the dispersion liquid=50/50), and the mixture is put in a sand grinder of 400 ml capacity (manufactured by Igarashi Kikai) in which a disk rotated at a peripheral speed of 5 m/second for 10 hours. The temperature of the internal atmosphere of the sand grinder is maintained at 20° to 25° C. After the pulverization is completed, the mixture is subjected to pressure filtration thereby obtaining about 100 g of a pulverized Trifluron dispersion liquid. It is possible to recover about 95 wt % of the Trifluron by washing the separated media with 60 g of water twice.

As shown in Table 17, 90 wt % of the particles in the pulverized Trifluron have a particle diameter of 0.5 micron or less.

TABLE 17

| Dispersion of Trifluron | Size Distribution (wt %) |
|---|---|
| 1.0 micron or more | 0 |
| 1.0–0.8 | 5 |
| 0.8–0.5 | 5 |
| 0.5–0.2 | 38 |
| 0.2 micron or less | 52 |

EXAMPLE 21

60 g of Bensultap powder (insecticide), 3 g of a dispersing agent represented by the formula

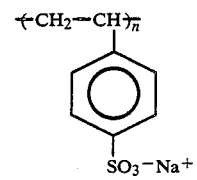

(molecular weight: about 50,000), 50 g of water and 120 g of glass beads (media) of 0.1 to 0.2 mm diameter are mixed (the ratio by volume of the media to the dispersion liquid=50/50), and the mixture is put in a sand grinder of 400 ml capacity (manufactured by Igarashi Kikai) in which a disk rotated at a peripheral speed of 6 m/second for 8 hours. The temperature of the internal atmosphere of the sand grinder is maintained at 20° to 25° C. After the pulverization is completed, the mixture is subjected to pressure filtration thereby obtaining about 100 g of a pulverized Bensultap dispersion liquid. It is possible to recover about 95 wt % of the Bensultap by washing the separated media with 50 g of water twice.

As shown in Table 18, 89 wt % Of the particles in the pulverized Bensultap have a particle diameter of 0.5 micron or less.

TABLE 18

| Dispersion of Bensultap | Size Distribution (wt %) |
|---|---|
| 1.0 micron or more | 0 |
| 1.0–0.8 | 3 |
| 0.8–0.5 | 8 |
| 0.5–0.2 | 40 |
| 0.2 micron or less | 49 |

EXAMPLE 22

60 g of Buprofezin powder (insecticide), 3 g of a dispersing agent represented by the formula

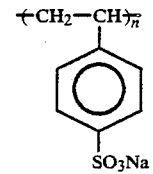

(molecular weight: about 100,000), 50 g of water and 120 g of glass beads (media) of 0.1 to 0.2 mm diameter are mixed (the ratio by volume of the media to the dispersion liquid=50/50), and the mixture is put in a sand grinder of 400 ml capacity (manufactured by Igarashi Kikai) in which a disk rotated at a peripheral speed of 7 m/second for 5 hours. The temperature of the internal atmosphere of the sand grinder is maintained at 20° to 25° C. After the pulverization is completed, the mixture is subjected to pressure filtration thereby obtaining about 100 g of a pulverized Buprofezin dispersion liquid. It is possible to recover about 90 wt % of the Buprofezin by washing the separated media with 60 g of water twice.

As shown in Table 19, 95 wt % of the particles in the pulverized Buprofezin have a particle diameter of 0.5 micron or less.

TABLE 19

| Dispersion of Buprofezin | Size Distribution (wt %) |
| --- | --- |
| 1.0 micron or more | 0 |
| 1.0–0.8 | 2 |
| 0.8–0.5 | 3 |
| 0.5–0.2 | 40 |
| 0.2 micron or less | 55 |

EXAMPLE 23

60 g of Ciromazine powder (insecticide), 3 g of a dispersing agent represented by the formula

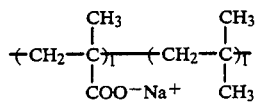

(molecular weight: about 70,000), 50 g of water and 120 g of glass beads (media) of 0.1 to 0.2 mm diameter are mixed (the ratio by volume of the media to the dispersion liquid=50/50), and the mixture is put in a sand grinder of 400 ml capacity (manufactured by Igarashi Kikai) in which a disk rotated at a peripheral speed of 8 m/second for 5 hours. The temperature of the internal atmosphere of the sand grinder is maintained at 20° to 25° C. After the pulverization is completed, the mixture is subjected to pressure filtration thereby obtaining about 100 g of a pulverized Ciromazine dispersion liquid. It is possible to recover about 90 wt % of the Ciromazine by washing the separated media with 50 g of water twice.

As shown in Table 20, 95 wt % of the particles in the pulverized Ciromazine have a particle diameter of 0.5 micron or less.

TABLE 20

| Dispersion of Ciromazine | Size Distribution (wt %) |
| --- | --- |
| 1.0 micron or more | 0 |
| 1.0–0.8 | 0 |
| 0.8–0.5 | 5 |
| 0.5–0.2 | 40 |
| 0.2 micron or less | 55 |

EXAMPLE 24

60 g of Fenbutatin-oxide powder (miticide), 3 g of a dispersing agent represented by the formula

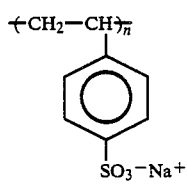

(molecular weight: about 10,000), 60 g of water and 120 g of glass beads (media) of 0.1 to 0.2 mm diameter are mixed (the ratio by volume of the media to the dispersion liquid=50/50), and the mixture is put in a sand grinder of 400 ml capacity (manufactured by Igarashi Kikai) in which a disk rotated at a peripheral speed of 6 m/second for 6 hours. The temperature of the internal atmosphere of the sand grinder is maintained at 20° to 25° C. After the pulverization is completed, the mixture is subjected to pressure filtration thereby obtaining about 100 g of a pulverized Fenbutatin-oxide dispersion liquid. It is possible to recover about 90 wt % of the Fenbutatin-oxide by washing the separated media with 50 g of water twice.

As shown in Table 21, 95 wt % of the particles in the pulverized Fenbutatin-oxide have a particle diameter of 0.5 micron or less.

TABLE 21

| Dispersion of Fenbutatin-oxide | Size Distribution (wt %) |
| --- | --- |
| 1.0 micron or more | 0 |
| 1.0–0.8 | 0 |
| 0.8–0.5 | 5 |
| 0.5–0.2 | 40 |
| 0.2 micron or less | 55 |

EXAMPLE 25

60 g of Azocyclotin powder (miticide), 3 g of a dispersing agent represented by the formula

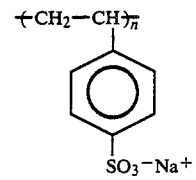

(molecular weight: about 200,000), 60 g of water and 130 g of glass beads (media) of 0.1 to 0.2 mm diameter are mixed (the ratio by volume of the media to the dispersion liquid=50/50), and the mixture is put in a sand grinder of 400 ml capacity (manufactured by Igarashi Kikai) in which a disk rotated at a peripheral speed of 8 m/second for 5 hours. The temperature of the internal atmosphere of the sand grinder is maintained at 20° to 25° C. After the pulverization is completed, the mixture is subjected to pressure filtration thereby obtaining about 100 g of a pulverized Azocylotin dispersion liquid. It is possible to recover about 90 wt % of the Azocylotin by washing the separated media with 20 g of water twice.

As shown in Table 22, 89 wt % of the particles in the pulverized Azocyclotin have a particle diameter of 0.5 micron or less.

TABLE 22

| Dispersion of Azocylotin | Size Distribution (wt %) |
| --- | --- |
| 1.0 micron or more | 0 |
| 1.0–0.8 | 0 |
| 0.8–0.5 | 11 |
| 0.5–0.2 | 40 |
| 0.2 micron or less | 49 |

EXAMPLE 26

60 g of Oxycarboxin powder (insecticide), 3 g of a dispersing agent represented by the formula

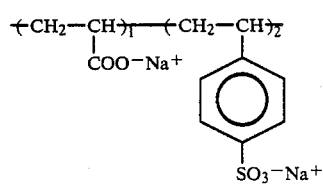

(molecular weight: about 100,000), 50 g of water and 120 g of glass beads (media) of 0.1 to 0.2 mm diameter are mixed (the ratio by volume of the media of the dispersion liquid=50/50), and the mixture is put in a sand grinder of 400 ml capacity (manufactured by Igarashi Kikai) in which a disk rotated at a peripheral speed of 8 m/second for 5 hours. The temperature of the internal atmosphere of the sand grinder is maintained at 20° to 25° C. After the pulverization is completed, the mixture is subjected to pressure filtration thereby obtaining about 100 g of a pulverized Oxycarboxin dispersion liquid. It is possible to recover about 95 wt % of the Oxycarboxin by washing the separated media with 30 g of water twice.

As shown in Table 23, 96 wt % of the particles in the pulverized Oxycarboxin have a particle diameter of 0.5 micron or less.

TABLE 23

| Dispersion of Oxycarboxin | Size Distribution (wt %) |
| --- | --- |
| 1.0 micron or more | 0 |
| 1.0–0.8 | 0 |
| 0.8–0.5 | 4 |
| 0.5–0.2 | 40 |
| 0.2 micron or less | 56 |

EXAMPLE 27

60 g of Ethirimol powder (germicide), 3 g of a dispersing agent represented by the formula

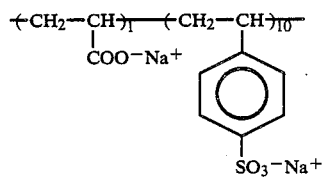

(molecular weight: about 100,000), 50 g of water and 120 g of glass beads (media) of 0.1 to 0.2 mm diameter are mixed (the ratio by volume of the media to the dispersion liquid=50/50), and the mixture is put in a sand grinder of 400 ml capacity (manufactured by Igarashi Kikai) in which a disk rotated at a peripheral speed of 10 m/second for 3 hours. The temperature of the internal atmosphere of the sand grinder is maintained at 20° to 25° C. After the pulverization is completed, the mixture is subjected to pressure filtration thereby obtaining about 100 g of a pulverized Ethirimol dispersion liquid. It is possible to recover about 95 wt % of the Ethirimol by washing the separated media with 40 g of water twice.

As shown in Table 24, 90 wt % of the particles in the pulverized Ethirimol have a particle diameter of 0.5 micron or less.

TABLE 24

| Dispersion of Ethirimol | Size Distribution (wt %) |
| --- | --- |
| 1.0 micron or more | 0 |
| 1.0–0.8 | 5 |
| 0.8–0.5 | 5 |
| 0.5–0.2 | 40 |
| 0.2 micron or less | 50 |

EXAMPLE 28

60 g of Bayleton powder (germicide), 3 g of a dispersing agent represented by the formula

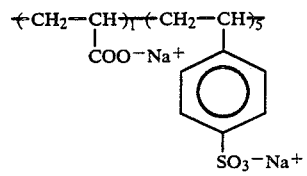

molecular weight: about 50,000), 60 g of water and 120 g of glass beads (media) of 0.1 to 0.2 mm diameter are mixed (the ratio by volume of the media to the dispersion liquid=50/50), and the mixture is put in a sand grinder of 400 ml capacity (manufactured by Igarashi Kikai) in which a disk rotated at a peripheral speed of 10 m/second for 3 hours. The temperature of the internal atmosphere of the sand grinder is maintained at 20° to 25° C. After the pulverization is completed, the mixture is subjected to pressure filtration thereby obtaining about 100 g of a pulverized Bayleton dispersion liquid. It is possible to recover about 90 wt % of the Bayleton by washing the separated media with 50 g of water twice.

As shown in Table 25, 95 wt % of the particles in the pulverized Bayleton have a particle diameter of 0.5 micron or less.

TABLE 25

| Dispersion of Bayleton | Size Distribution (wt %) |
| --- | --- |
| 1.0 micron or more | 0 |
| 1.0–0.8 | 0 |
| 0.8–0.5 | 5 |
| 0.5–0.2 | 30 |
| 0.2 micron or less | 65 |

EXAMPLE 29

60 g of Rubigan powder (germicide), 3 g of a dispersing agent represented by the formula

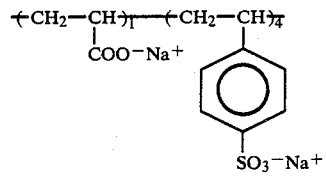

(molecular weight: about 100,000), 50 g of water and 120 g of glass beads (media) of 0.1 to 0.2 mm diameter are mixed (the ratio by volume of the media to the dispersion liquid=50/50), and the mixture is put in a sand grinder of 400 ml capacity (manufactured by Igarashi Kikai) in which a disk rotated at a peripheral speed of 11 m/second for 2 hours. The temperature of the internal atmosphere of the sand grinder is maintained at 20° to 25° C. After the pulverization is completed, the mixture is subjected to pressure filtration thereby obtaining about 100 g of a pulverized Rubigan dispersion liquid. It is possible to recover about 95 wt % of the Rubigan by washing the separated media with 20 g of water twice.

As shown in Table 26, 99 wt % of the particles in the pulverized Rubigan have a particle diameter of 0.5 micron or less.

TABLE 26

| Dispersion of Rubigan | Size Distribution (wt %) |
|---|---|
| 1.0 micron or more | 0 |
| 1.0–0.8 | 0 |
| 0.8–0.5 | 1 |
| 0.5–0.2 | 30 |
| 0.2 micron or less | 69 |

EXAMPLE 30

60 g of Sumilex powder (germicide), 3 g of a dispersing agent represented by the formula

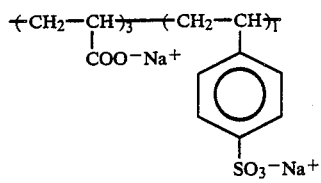

(molecular weight: about 70,000), 50 g of water and 120 g of glass beads (media) of 0.1 to 0.2 mm diameter are mixed (the ratio by volume of the media to the dispersion liquid=50/50), and the mixture is put in a sand grinder of 400 ml capacity (manufactured by Igarashi Kikai) in which a disk rotated at a peripheral speed of 15 m/second for 1 hour. The temperature of the internal atmosphere of the sand grinder is maintained at 20° to 25° C. After the pulverization is completed, the mixture is subjected to pressure filtration thereby obtaining about 100 g of a pulverized Sumilex dispersion liquid. It is possible to recover about 95 wt % of the Sumilex by washing the separated media with 40 g of water twice.

As shown in Table 27, 94 wt % of the particles in the pulverized Sumilex have a particle diameter of 0.5 micron or less.

TABLE 27

| Dispersion of Sumilex | Size Distribution (wt %) |
|---|---|
| 1.0 micron or more | 0 |
| 1.0–0.8 | 2 |
| 0.8–0.5 | 4 |
| 0.5–0.2 | 30 |
| 0.2 micron or less | 64 |

EXAMPLE 31

60 g of Vinclozolin powder (germicide), 3 g of a dispersing agent represented by the formula

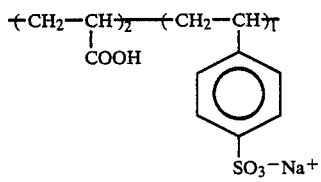

(molecular weight: about 100,000), 50 g of water and 120 g of glass beads (media) of 0.1 to 0.2 mm diameter are mixed (the ratio by volume of the media to the dispersion liquid=50/50), and the mixture is put in a sand grinder of 400 ml capacity (manufactured by Igarashi Kikai) in which a disk rotated at a peripheral speed of 12 m/second for 1 hour. The temperature of the internal atmosphere of the sand grinder is maintained at 20° to 25° C. After the pulverization is completed, the mixture is subjected to pressure filtration thereby obtaining about 100 g of a pulverized Vinclozolin dispersion liquid. It is possible to recover about 90 wt % of the Vinclozolin by washing the separated media with 20 g of water twice.

As shown in Table 28, 92 wt % of the particles in the pulverized Vinclozolin have a particle diameter of 0.5 micron or less.

TABLE 28

| Dispersion of Vinclozolin | Size Distribution (wt %) |
|---|---|
| 1.0 micron or more | 0 |
| 1.0–0.8 | 0 |
| 0.8–0.5 | 8 |
| 0.5–0.2 | 30 |
| 0.2 micron or less | 62 |

EXAMPLE 32

60 g of Cultar powder (germicide), 3 g of a dispersing agent represented by the formula

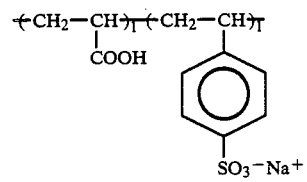

(molecular weight: about 10,000), 50 g of water and 120 g of glass beads (media) of 0.1 to 0.2 mm diameter are mixed (the ratio by volume of the media to the dispersion liquid=50/50), and the mixture is put in a sand grinder of 400 ml capacity (manufactured by Igarashi Kikai) in which a disk rotated at a peripheral speed of 15 m/second for 1 hour. The temperature of the internal atmosphere of the sand grinder is maintained at 20° to 25° C. After the pulverization is completed, the mixture is subjected to pressure filtration thereby obtaining about 100 g of a pulverized Cultar dispersion liquid. It is possible to recover about 98 wt % of the Cultar by washing the separated media with 50 g of water twice.

As shown in Table 29, 91 wt % of the particles in the pulverized Cultar have a particle diameter of 0.5 micron or less.

TABLE 29

| Distribution of Cultar | Size Distribution (wt %) |
|---|---|
| 1.0 micron or more | 0 |
| 1.0–0.8 | 1 |
| 0.8–0.5 | 8 |
| 0.5–0.2 | 40 |
| 0.2 micron or less | 51 |

EXAMPLE 33

60 g of Vigil powder (germicide), 3 g of a dispersing agent represented by the formula

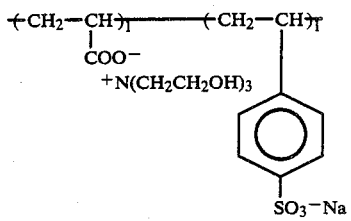

(molecular weight: about 20,000), 50 g of water and 120 g of glass beads (media) of 0.1 to 0.2 mm diameter are mixed (the ratio by volume of the media to the dispersion liquid=50/50), and the mixture is put in a sand grinder of 400 ml capacity (manufactured by Igarashi Kikai) in which a disk rotated at a peripheral speed of 6 m/second for 5 hours. The temperature of the internal atmosphere of the sand grinder is maintained at 20° to 25° C. After the pulverization is completed, the mixture is subjected to pressure filtration thereby obtaining about 100 g of a pulverized Vigil dispersion liquid. It is possible to recover about 90 wt % of the Vigil by washing the separated media with 50 g of water twice.

As shown in Table 30, 96 wt % of the particles in the pulverized Vigil have a particle diameter of 0.5 micron or less.

TABLE 30

| Dispersion of Vigil | Size Distribution (wt %) |
| --- | --- |
| 1.0 micron or more | 0 |
| 1.0–0.8 | 0 |
| 0.8–0.5 | 4 |
| 0.5–0.2 | 40 |
| 0.2 micron or less | 56 |

EXAMPLE 34

60 g of Aliette powder (germicide), 3 g of a dispersing agent represented by the formula

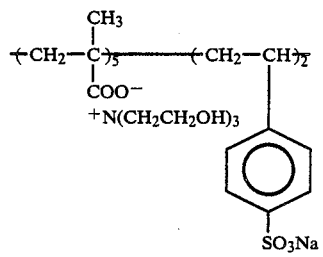

(molecular weight: about 50,000), 50 g of water and 120 g of glass beads (media) of 0.1 to 0.2 mm diameter are mixed (the ratio by volume of the media to the dispersion liquid=50/50), and the mixture is put in a sand grinder of 400 ml capacity (manufactured by Igarashi Kikai) in which a disk rotated at a peripheral speed of 8 m/second for 2 hours. The temperature of the internal atmosphere of the sand grinder is maintained at 20° to 25° C. After the pulverization is completed, the mixture is subjected to pressure filtration thereby obtaining about 100 g of a pulverized Aliette dispersion liquid. It is possible to recover about 98 wt % of the Aliette by washing the separated media with 50 g of water twice.

As shown in Table 31, 88 wt % of the particles in the pulverized Aliette have a particle diameter of 0.5 micron or less.

TABLE 31

| Dispersion of Aliette | Size Distribution (wt %) |
| --- | --- |
| 1.0 micron or more | 0 |
| 1.0–0.8 | 2 |
| 0.8–0.5 | 10 |
| 0.5–0.2 | 40 |
| 0.2 micron or less | 48 |

EXAMPLE 35

60 g of Tricylazole powder (germicide), 3 g of a dispersing agent represented by the formula

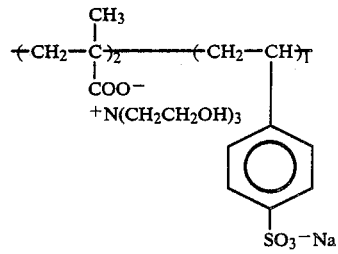

(molecular weight: about 150,000), 60 g of water and 120 g of glass beads (media) of 0.1 to 0.2 mm diameter are mixed (the ratio by volume of the media to the dispersion liquid=50/50), and the mixture is put in a sand grinder of 400 ml capacity (manufactured by Igarashi Kikai) in which a disk rotated at a peripheral speed of 15 m/second for 1 hour. The temperature of the internal atmosphere of the sand grinder is maintained at 20° to 25° C. After the pulverization is completed, the mixture is subjected to pressure filtration thereby obtaining about 100 g of a pulverized Tricylazole dispersion liquid. It is possible to recover about 99 wt % of the Tricylazole by washing the separated media with 20 g of water twice.

As shown in Table 32, 98 wt % of the particles in the pulverized Tricylazole have a particle diameter of 0.5 micron or less.

TABLE 32

| Dispersion of Tricylazole | Size Distribution (wt %) |
| --- | --- |
| 1.0 micron or more | 0 |
| 1.0–0.8 | 0 |
| 0.8–0.5 | 2 |
| 0.5–0.2 | 53 |
| 0.2 micron or less | 45 |

EXAMPLE 36

60 g of Fenoxaprop-ethyl powder (herbicide), 3 g of a dispersing agent represented by the formula

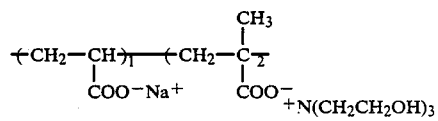

(molecular weight: about 180,000), 50 g of water and 120 g of glass beads (media) of 0.1 to 0.2 mm diameter are mixed (the ratio by volume of the media to the dispersion liquid=50/50), and the mixture is put in a sand grinder of 400 ml capacity (manufactured by Igarashi Kikai) in which a disk rotated at a peripheral speed of 15 m/second for 1 hour. The temperature of the internal atmosphere of the sand grinder is maintained at 20° to 25° C. After the pulverization is completed, the mixture is subjected to pressure filtration thereby obtaining about 100 g of a pulverized Fenoxaprop-ethyl dispersion liquid. It is possible to recover about 98 wt % of the Fenoxapropethyl by washing the separated media with 25 g of water twice.

As shown in Table 33, 92 wt % of the particles in the pulverized Fenoxaprop-ethyl have a particle diameter of 0.5 micron or less.

TABLE 33

| Dispersion of Fenoxaprop-ethyl | Size Distribution (wt %) |
|---|---|
| 1.0 micron or more | 0 |
| 1.0–0.8 | 4 |
| 0.8–0.5 | 4 |
| 0.5–0.2 | 50 |
| 0.2 micron or less | 42 |

EXAMPLE 37

60 g of Dimefuron powder (herbicide), 3 g of a dispersing agent represented by the formula

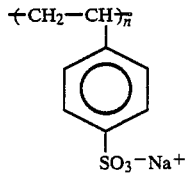

SO$_3^-$Na$^+$ (molecular weight: about 300,000), 50 g of water and 120 g of glass beads (media) of 0.1 to 0.2 mm diameter are mixed (the ratio by volume of the media to the dispersion liquid = 50/50), and the mixture is put in a sand grinder of 400 ml capacity (manufactured by Igarashi Kikai) in which a disk rotated at a peripheral speed of 15 m/second for 1 hour. The temperature of the internal atmosphere of the sand grinder is maintained at 20° to 25° C. After the pulverization is completed, the mixture is subjected to pressure filtration thereby obtaining about 100 g of a pulverized Dimefuron dispersion liquid. It is possible to recover about 98 wt % of the Dimefuron by washing the separated media with 15 g of water twice.

As shown in Table 34, 98 wt % of the particles in the pulverized Dimefuron have a particle diameter of 0.5 micron or less.

TABLE 34

| Dispersion of Dimefuron | Size Distribution (wt %) |
|---|---|
| 1.0 micron or more | 0 |
| 1.0–0.8 | 0 |
| 0.8–0.5 | 2 |
| 0.5–0.2 | 30 |
| 0.2 micron or less | 68 |

EXAMPLE 38

60 g of Chlorsulfuron powder (herbicide), 4 g of a dispersing agent represented by the formula

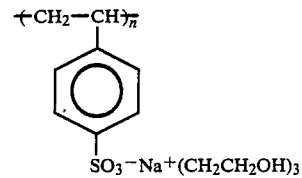

SO$_3^-$Na$^+$(CH$_2$CH$_2$OH)$_3$ (molecular weight: about 100,000), 50 g of water and 120 g of glass beads (media) of 0.1 to 0.2 mm diameter are mixed (the ratio by volume of the media to the dispersion liquid = 50/50), and the mixture is put in a sand grinder of 400 ml capacity (manufactured by Igarashi Kikai) in which a disk rotated at a peripheral speed of 12 m/second for 1 hour. The temperature of the internal atmosphere of the sand grinder is maintained at 20° to 25° C. After the pulverization is completed, the mixture is subjected to pressure filtration thereby obtaining about 110 g of a pulverized Chlorsulfuron dispersion liquid. It is possible to recover about 98 wt % of the Chlorsulfuron by washing the separated media with 25 g of water twice.

As shown in Table 35, 99 wt % of the particles in the pulverized Chlorsulfuron have a particle diameter of 0.5 micron or less.

TABLE 35

| Dispersion of Chlorsulfuron | Size Distribution (wt %) |
|---|---|
| 1.0 micron or more | 0 |
| 1.0–0.8 | 0 |
| 0.8–0.5 | 1 |
| 0.5–0.2 | 20 |
| 0.2 micron or less | 79 |

EXAMPLE 39

60 g of Sulfometuron Methyl powder (herbicide), 3 g of a dispersing agent represented by the formula

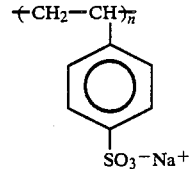

SO$_3^-$Na$^+$ (molecular weight: about 500,000), 50 g of water and 120 g of glass beads (media) of 0.1 to 0.2 mm diameter are mixed (the ratio by volume of the media to the dispersion liquid = 50/50), and the mixture is put in a sand grinder of 400 ml capacity (manufactured by Igarashi Kikai) in which a disk rotated at a peripheral speed of 11 m/second for 1 hour. The temperature of the internal atmosphere of the sand grinder is maintained at 20° to 25° C. After the pulverization is completed, the mixture is subjected to pressure filtration thereby obtaining about 110 g of a pulverized Sulfometuron Methyl dispersion liquid. It is possible to recover about 99 wt % of the Sulfometuron Methyl by washing the separated media with 15 g of water twice.

As shown in Table 36, 91 wt % of the particles in the pulverized Sulfometuron Methyl have a particle diameter of 0.5 micron or less.

TABLE 36

| Dispersion of Sulfometuron Methyl | Size Distribution (wt %) |
|---|---|
| 1.0 micron or more | 0 |
| 1.0–0.8 | 0 |
| 0.8–0.5 | 9 |
| 0.5–0.2 | 40 |
| 0.2 micron or more | 51 |

EXAMPLE 40

The Vinclozolin dispersion liquid obtained in Example 31 (according to this invention) and Vinclozolin dispersion liquids (conventional products) having particle diameter distributions shown in Table 37 were used to carry out a biological experiment according to the following method. The results of the experiment are shown in Table 38.

TABLE 37

| Dispersion of Vinclozolin (Prior Art) | Size Distribution (wt %) |
|---|---|
| 1.0 micron or more | 70 |
| 1.0–0.8 | 26 |
| 0.8–0.5 | 4 |
| 0.5–0.2 | 0 |
| 0.2 micron or less | 0 |

(Method of Experiment)

Mandarin oranges were immersed in a suspension liquid of gray mold spores for six hours. Following that, various concentration of each of the Vinclozolin dispersion liquid of this invention and the conventional Vinclozolin dispersion liquids were sprayed on the treated mandarin oranges (1 ml/mandarin orange). The thus treated mandarin oranges were then stored at 27° C. for two weeks to investigate the control effects of these dispersion liquids. Evaluation of the control effect was performed in accordance with the following evaluation criteria.

| Evaluation Criteria: | |
|---|---|
| Fruit Infection | Evaluation |
| Healthy Fruit | 5 |
| 20% Infection | 4 |
| 50% Infection | 3 |
| 80% Infection | 2 |
| 100% Infection | 1 |

TABLE 38

| Concentration of Vinclozolin | Example 31 (Inventive Product) | Conventional Product |
|---|---|---|
| 160 ppm | 5 | 5 |
| 80 | 5 | 4 |
| 40 | 5 | 3 |
| 20 | 5 | 2 |
| 10 | 5 | 1 |
| 5 | 4 | 1 |
| Non-treatment | 1 | 1 |

EXAMPLE 41

The Fenoxaprop-ethyl dispersion liquid obtained in Example 36 (according to this invention) and 50% Fenoxaprop-ethyl water-dispersible powder (commercial product) were used to carry out a biological experiment according to the following method. The results were shown in Table 39.

(Method of the Experiment)

After crab grasses were grown until they became 3 to 4 leaf stages of 7 cm height, each of the dispersion liquids of the present invention and the commercial product was sprayed on the grown grasses in order to investigate the herbicidal effects of these agents. Evaluation of the herbicidal effect was performed by measuring the raw weight of the portions exposed above the ground of the grasses of the treated division and that of the non-treated division in order to obtain a herbicidal percentage. The amount of each aqueous dilute sprayed was adjusted to 20 1/are.

TABLE 39

| Amount of Herbicide | Example 36 (Inventive Product) | 50% Fenoxaprop-ethyl Water-dispersible Powder (Commercial Product) |
|---|---|---|
| 50 g/are | 100% | 50% |
| 40 " | 90 | 39 |
| 30 " | 75 | 22 |
| 20 " | 70 | 20 |
| 10 " | 40 | 10 |

EXAMPLE 42

The Azocyclotin dispersion liquid obtained in Example 25 (according to this invention) and 50% Azocyclotin water-dispersible powder (commercial product) were used to carry out a biological experiment according to the following method. The results of the experiment are shown in Table 40.

(Method of the Experiment)

Thirty female adults of two-spotted mites were implanted in each hericol leaf disk of 50 cm × 50 cm before they were left at 25° C. for one day. Following that, various concentration of each of the dispersion liquid of this invention and the commercial product (0.3 ml/disk) were repeatedly sprayed 10 times. Three days after the spraying, the ratio of the number of mites killed in the treated division to that of mites killed in the non-treated division was obtained as a miticidal rate.

TABLE 40

| Concentration of Azocyclotin | Example 25 (Inventive Product) | 50% Azocyclotin Water-dispersible Powder (Commercial Product) |
|---|---|---|
| 500 ppm | 100% | 80% |
| 250 ppm | 100 | 74 |
| 125 ppm | 100 | 54 |
| 62.5 ppm | 90 | 45 |
| 31.75 ppm | 85 | 30 |

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A suspension for agricultural use, comprising:
   (i) a germicidal fine powder comprising at least 50 wt.% of particles with a diameter of 0.5 micron or less; and (ii) an adjuvant comprising a polyoxyalkylene-type nonionic surface active agent or a polyoxyalkylene alkyl or alkylaryl ether phosphate or its salt, or mixtures thereof.

2. The suspension of claim 1, wherein said polyoxyalkylene-type nonionic surface active agent is selected from the group consisting of
   (a) products obtained by reacting an alkylene oxide with a mixture of a fatty acid triglyceride and a polyhydric alcohol;
   (b) polyoxyalkylene alkyl or alkenyl ethers, wherein said alkyl or alkenyl group contains 4–20 carbon atoms inclusive;
   (c) polyoxyalkylene mono- or di-alkyl or aryl phenyl ethers, wherein said alkyl group contains 4–18 carbon atoms inclusive and said aryl group is a benzyl, phenyl or styryl group;
   (d) polyoxyalkylene sorbitan fatty acid esters, wherein the fatty acid comprises 8–22 carbon atoms inclusive;
   (e) polyoxyalkylene sorbitol fatty acid esters, wherein the fatty acid comprises 8–22 carbon atoms inclusive;
   (f) polyoxyalkylene sorbitol alkyl ethers, wherein said alkyl group comprises 8–22 carbon atoms inclusive;
   (g) polyoxyalkylene alkyl or alkenyl amines, wherein said alkyl or alkenyl group comprises 4–22 carbon atoms;
   (h) polyoxyethylene/polyoxypropylene block polymers;
   or mixtures thereof.

3. The suspension of claim 1, wherein the weight ratio of said germicidal fine powder to said adjuvant is from 1.0:0.05 to 1.0:20.0.

4. The suspension of claim 3, wherein said ratio is from 1.0:0.2 to 1.0:20.0.

5. The suspension of claim 3, wherein said ratio is 1.0:0.5 to 1.0:15.0.

6. The suspension of claim 1, further comprising a dispersion agent, a water-soluble thickener, an antifoaming agent, a decomposition-preventing agent, an agglutination-preventing agent, a drift-preventing agent and mixtures thereof.

* * * * *